United States Patent
Shue et al.

(10) Patent No.: US 7,507,564 B2
(45) Date of Patent: Mar. 24, 2009

(54) TIACUMICIN PRODUCTION

(75) Inventors: Youe-Kong Shue, Carlsbad, CA (US);
Chi-Jen Frank Du, Taipei (TW);
Ming-Hsi Chiou, Taoyuan (TW);
Mei-Chiao Wu, Taoyuan (TW);
Yuan-Ting Chen, Hualien (TW);
Franklin W. Okumu, San Diego, CA (US); Jonathan James Duffield, San Diego, CA (US)

(73) Assignee: Optimer Pharmaceuticals, Inc., San Diego, CA (US)

( * ) Notice: Subject to any disclaimer, the term of this patent is extended or adjusted under 35 U.S.C. 154(b) by 272 days.

(21) Appl. No.: 10/520,863

(22) PCT Filed: Jul. 15, 2003

(86) PCT No.: PCT/US03/21977

§ 371 (c)(1),
(2), (4) Date: Jul. 13, 2005

(87) PCT Pub. No.: WO2004/014295

PCT Pub. Date: Feb. 19, 2004

(65) Prior Publication Data
US 2006/0257981 A1    Nov. 16, 2006

(51) Int. Cl.
*A61K 31/70* (2006.01)
(52) U.S. Cl. .................. 435/180; 435/118; 435/119; 435/174; 435/117
(58) Field of Classification Search .................. None
See application file for complete search history.

(56) References Cited

U.S. PATENT DOCUMENTS

| 3,978,211 | A | * | 8/1976 | Coronelli et al. | ............ 424/120 |
| 4,632,902 | A | * | 12/1986 | Waters et al. | .................. 435/29 |
| 4,918,174 | A | * | 4/1990 | McAlpine et al. | ............ 536/7.1 |
| 7,067,544 | B2 | * | 6/2006 | Hoefle et al. | ................ 514/365 |

OTHER PUBLICATIONS

Hochlowski et al., Tiacumicins, a novel complex of 18-membered macrolides. II. Isolation and structure determination. J. Antibiotics 40: 575-588, 1987.*
Demain et al. "Manual of Industrial Microbiology and Biotechnology", American Society for Microbiology, Washington D.C., 1986, pp. 123-126.
Theriault, Robert J., et al., "Tiacumicins, A Novel Complex of 18-Membered Macrolide Antibiotics" J. Antibiotics, vol. XL, 5, pp. 567-574, 1987.

* cited by examiner

*Primary Examiner*—Irene Marx
(74) *Attorney, Agent, or Firm*—Cohen Pontani Lieberman & Pavane LLP

(57) ABSTRACT

Methods, processes and materials for the production and recovery of Tiacumicins produced by culturing a microorganism belonging to the species *Dactylosporangium aurantiacum* subspecies *hamdenensis* having the ability to produce and accumulate one or more Tiacumicin in a nutrient medium comprising a carbon source, a nitrogen source, trace elements such as inorganic salts, and an adsorbent, wherein said nitrogen source comprises fish powder, and wherein said Tiacumicin is produced in a yield greater than about 50 mg/L broth.

10 Claims, 3 Drawing Sheets

TIACUMICIN PRODUCTION

BACKGROUND OF THE INVENTION

Tiacumicins are a family of structurally related compounds that contain the 18-membered macrolide ring shown below.

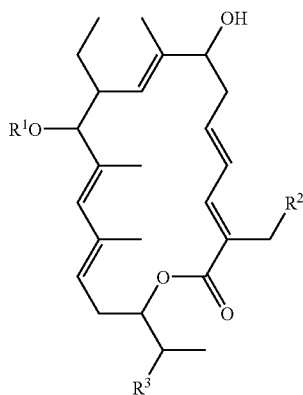

At present, several distinct Tiacumicins have been identified and six of these (Tiacumicin A-F) are defined by their particular pattern of substituents $R^1$, $R^2$, and $R^3$ (U.S. Pat. No. 4,918,174; J. Antibiotics, 1987, 575-588).

The Lipiarmycins are a family of natural products closely related to the Tiacumicins. Two members of the Lipiarmycin family (A3 and B3) are identical to Tiacumicins B and C respectively (J. Antibiotics, 1988, 308-315; J. Chem. Soc. Perkin Trans I, 1987, 1353-1359).

The Tiacumicins and the Lipiarmycins have been characterized by numerous physical methods. The reported chemical structures of these compounds are based on spectroscopy (UV-vis, IR and $^1$H and $^{13}$C NMR), mass spectrometry and elemental analysis (See for example: J. Antibiotics, 1987, 575-588; J. Antibiotics, 1983, 1312-1322).

Tiacumicins are produced by bacteria, including *Dactylosporangium aurantiacum* subspecies *hamdenensis*, which may be obtained from the ARS Patent Collection of the Northern Regional Research Center, United States Department of Agriculture, 1815 North University Street, Peoria, Ill. 61604, accession number NRRL 18085. The characteristics of strain AB 718C-41 are given in J. Antibiotics, 1987, 567-574 and U.S. Pat. No. 4,918,174.

Lipiarmycins are produced by bacteria including *Actinoplanes deccanensis* (U.S. Pat. No. 3,978,211). Taxonomical studies of type strain A/10655, which has been deposited in the ATCC under the number 21983, are discussed in J. Antibiotics, 1975, 247-25.

Tiacumicins, specifically Tiacumicin B, show activity against a variety of bacterial pathogens and in particular against *Clostridium difficile*, a Gram-positive bacterium (Antimicrob. Agents Chemother. 1991, 1108-1111). *Clostridium difficile* is an anaerobic spore-forming bacterium that causes an infection of the bowel. Diarrhea is the most common symptom but abdominal pain and fever may also occur. *Clostridium difficile* is a major causative agent of colitis (inflammation of the colon) and diarrhea that may occur following antibiotic intake. This bacterium is primarily acquired in hospitals and chronic care facilities. Because Tiacumicin B shows promising activity against *C. difficile*, it is expected to be useful in the treatment of bacterial infections, especially those of the gastrointestinal tract, in mammals. Examples of such treatments include but are not limited to treatment of colitis and treatment of irritable bowel syndrome. Tiacumicins may also find use for the treatment of gastrointestinal cancers.

Fermentation processes are used to obtain antibiotics, including Tiacumicins. Antibiotics may be produced by culturing a microorganism in a medium containing readily assimilated sources of carbon, nitrogen, and inorganic salts under submerged aerobic fermentation conditions, until a substantial amount of antibiotic activity is produced as deduced from in-process analyses. Because of rising worldwide demand for antibiotics, there is an ongoing need for improved methods to produce antibiotics.

SUMMARY OF THE INVENTION

Figure 1:
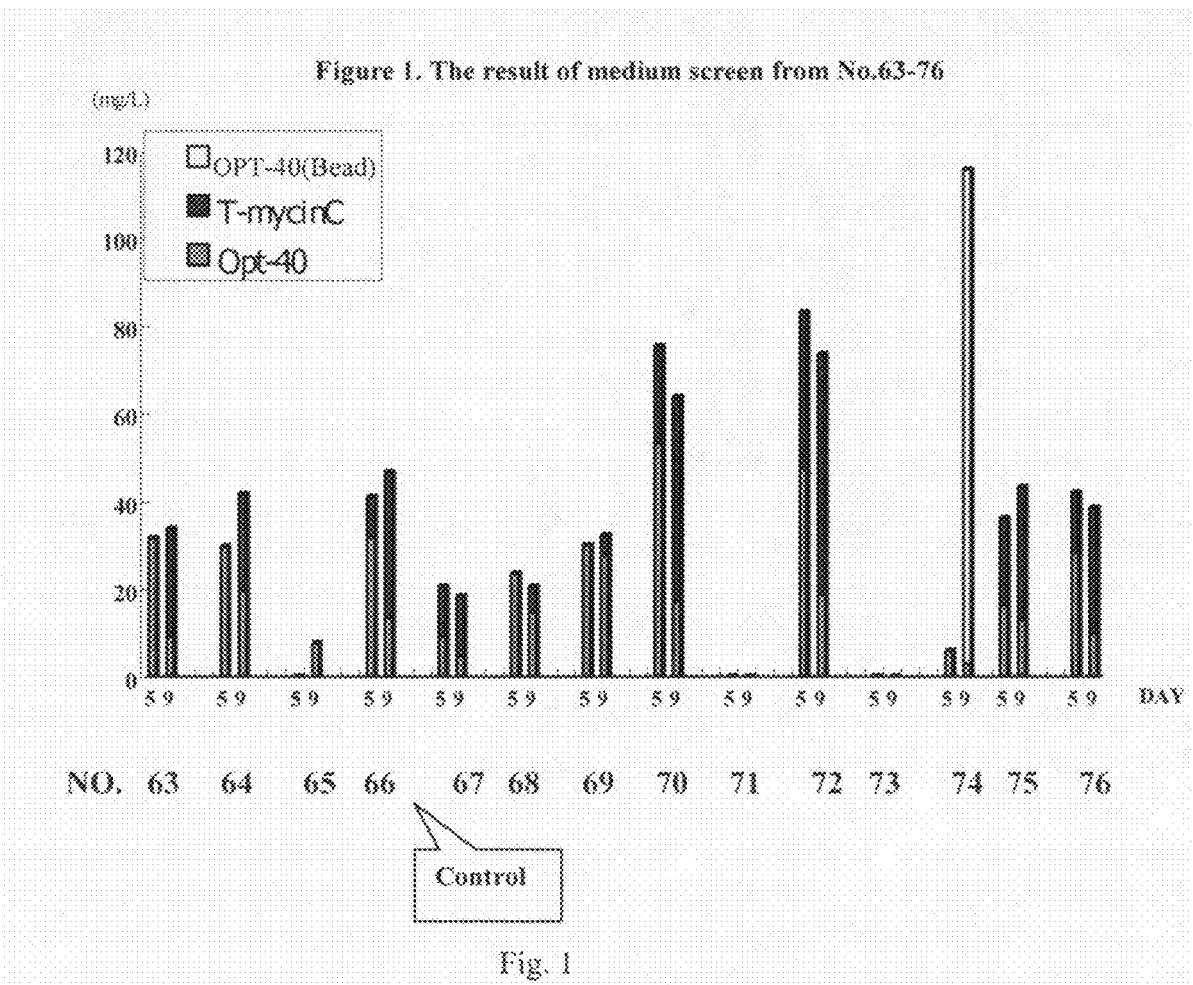
FIG. 1 shows an HPLC chromatogram of crude fermentation products produced according to Example 1; Tiacumicin B has a retention time of approximately 12.6 min.

The present invention presents methods, processes and materials for the production of Tiacumicins. The present invention also presents Tiacumicins produced using the fermentation methods, processes, and materials described herein.

One embodiment of the present invention comprises a process for producing Tiacumicins which comprises culturing a microorganism belonging to the species *Dactylosporangium aurantiacum* subspecies *hamdenensis* having the ability to produce Tiacumicins in a nutrient medium and accumulating at least one Tiacumicin in the nutrient medium, wherein the yield of at least one Tiacumicin is greater than about 50 mg/L broth.

In one embodiment of the invention, improved media and conditions for the fermentative production of Tiacumicin B are described. Thus, one embodiment of the present invention is a nutrient medium for production of Tiacumicins comprising a carbon source, a nitrogen source, trace elements such as inorganic salts, and an adsorbent, wherein said nitrogen source comprises fish powder, and wherein said nutrient medium is used to produce one or more Tiacumicin in a yield greater than about 50 mg/L broth.

In another embodiment of the invention, an improved recovery method, resin adsorption of Tiacumicin B is described.

Another embodiment of the invention involves using bacterial strains related to *Dactylosporangium aurantiacum* subspecies *hamdenensis*, as organisms for producing Tiacumicins. Thus, the present invention includes a Tiacumicin produced by culturing a microorganism belonging to the species *Dactylosporangium aurantiacum* subspecies *hamdenensis* having the ability to produce and accumulate one or more Tiacumicin in a nutrient medium comprising a carbon source, a nitrogen source, trace elements such as inorganic salts, and an adsorbent, wherein said nitrogen source comprises fish powder, and wherein said Tiacumicin is produced in a yield greater than about 50 mg/L broth.

Another embodiment of the invention involves the use of reverse phase medium pressure liquid chromatography and/or liquid/liquid partition and/or trituration for the purification of Tiacumicins from the crude fermentation product.

These improvements, alone or together, allow the fermentative production and recovery of Tiacumicin B in much improved yield (>50 mg/L broth).

DETAILED DESCRIPTION OF THE INVENTION

All patents, publications and patent applications referred to herein are hereby incorporated by reference in their entireties. Unless otherwise defined, all technical and scientific terms used herein have the same meaning as commonly understood by one of ordinary skill in the art to which this invention belongs. Exemplary methods and materials are described below. However, methods and materials similar or equivalent to those described herein can be also used to obtain variations of the present invention. The materials, methods, and examples are illustrative only and not intended to be limiting.

The compositions containing the Tiacumicins of the invention can be administered for prophylactic and/or therapeutic treatments. In therapeutic applications, the compositions are administered to a patient already suffering from an infection, as described above, in an amount sufficient to cure or at least partially arrest the symptoms of the infection. An amount adequate to accomplish this is defined as "therapeutically effective amount or dose." Amounts effective for this use will depend on the severity and course of the infection, previous therapy, the patient's health status and response to the drugs, and the judgment of the treating physician. In prophylactic applications, compositions containing the Tiacumicins of the invention are administered to a patient susceptible to or otherwise at risk of a particular infection. Such an amount is defined to be a "prophylactically effective amount or dose." In this use, the precise amounts again depend on the patient's state of health, weight, and the like.

Once improvement of the patient's conditions has occurred, a maintenance dose is administered if necessary. Subsequently, the dosage or the frequency of administration, or both, can be reduced, as a function of the symptoms, to a level at which the improved condition is retained. When the symptoms have been alleviated to the desired level, treatment can cease. Patients can, however, require intermittent treatment on a long-term basis upon any recurrence of the disease symptoms.

In general, a suitable effective dose of the Tiacumicins of the present invention will be in the range of 0.1 to 1000 milligrams (mg) per recipient per day, preferably in the range of 1 to 500 mg per day. The desired dosage is preferably presented in one, two, three, four or more subdoses administered at appropriate intervals throughout the day. These subdoses can be administered as unit dosage forms, for example, containing 5 to 1000 mg, preferably 10 to 200 mg of active ingredient per unit dosage form. Preferably, the compounds of the invention will be administered in amounts of between about 1.0 mg/kg to 250 mg/kg of patient body weight, between about one to four times per day.

A "pharmacological composition" refers to a mixture of one or more of the Tiacumicins described herein, or physiologically acceptable salts thereof, with other chemical components, such as physiologically acceptable carriers and/or excipients. The purpose of a pharmacological composition is to facilitate administration of a compound to an organism.

"Pharmaceutically acceptable salts" of the compounds of the invention include those derived from pharmaceutically acceptable inorganic and organic acids and bases. Examples of suitable acids include hydrochloric, hydrobromic, sulfuric, nitric, perchloric, fumaric, maleic, phosphoric, glycolic, gluconic, lactic, salicylic, succinic, toluene-p-sulfonic, tartaric, acetic, citric, methanesulfonic, formic, benzoic, malonic, naphthalene-2-sulfonic, benzenesulfonic, 1,2 ethanesulfonic acid (edisylate), galactosyl-D-gluconic acid, and the like. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and $N(C_1-C_4 \text{ alkyl})_4^+$ salts, and the like. Illustrative examples of some of these include sodium hydroxide, potassium hydroxide, choline hydroxide, sodium carbonate, and the like.

A "physiologically acceptable carrier" refers to a carrier or diluent that does not cause significant irritation to an organism and does not abrogate the biological activity and properties of the administered compound.

An "excipient" refers to an inert substance added to a pharmacological composition to further facilitate administration of a compound. Examples of excipients include but are not limited to, calcium carbonate, calcium phosphate, various sugars and types of starch, cellulose derivatives, gelatin, vegetable oils and polyethylene glycols.

The term "nutrient medium" as used herein describes a mixture of synthetic or naturally occurring ingredients. In general, a nutrient medium comprises a carbon source, a nitrogen source, trace elements such as inorganic salts, and optionally vitamins or other growth factors, and an adsorbent.

The term "broth" as used herein refers to the fluid culture medium as obtained during or after fermentation. Broth comprises a mixture of water, the desired antibiotic(s), unused nutrients, living or dead organisms, metabolic products, and the adsorbent with or without adsorbed product.

The term "Tiacumicin" as used herein refers to a family of compounds all of which comprise the 18-membered macrolide ring shown below:

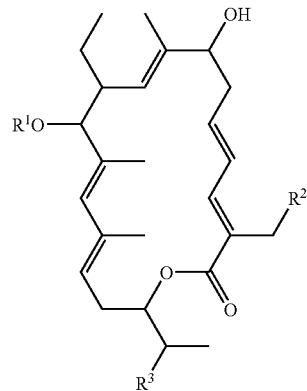

The term "Tiacumicin B" refers to molecule having the structure shown below:

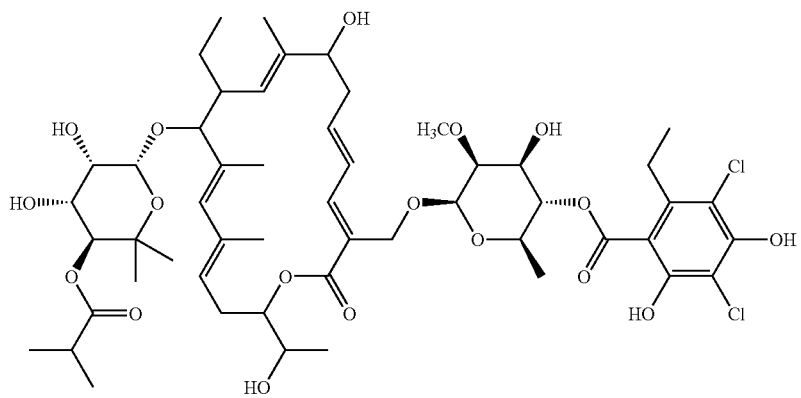

The term "yield" as used herein refers to an amount of crude Tiacumicin re-constituted in methanol to the same volume as the original fermentation broth. Yield is determined using standard HPLC techniques. Yield is reported in units of mg/L.

One embodiment of the invention comprises a process suitable for producing antibiotic agents, for example Tiacumicins, by submerged aerobic fermentation of the microorganism. One embodiment of such an organism is *Dactylosporangium aurantiacum* subspecies *hamdenensi*. According to one embodiment of the invention, Tiacumicins, for example Tiacumicin B, are recovered in exceptional yield (>100 mg/L broth) from the fermentation broth by resin absorption and eluted from the resin and mycelium by washing with solvents of various polarities. Purification may be furthered by solvent extraction and/or chromatographic separation such as Sephadex, silica gel, High-Performance Liquid Chromatography (HPLC) or reverse phase medium pressure liquid chromatography and/or recrystallization with one or more solvents and/or trituration with one or more solvents.

One microorganism employed in this invention was identified as belonging to the family Actinoplanaceae, genus *Dactylosporangium* (Journal of Antibiotics, 1987, p. 567-574 and U.S. Pat. No. 4,918,174). It has been designated *Dactylasporangium aurantiacum* subspecies *hamdenensis* 718C-41. The subculture was obtained from the ARS Patent Collection of the Northern Regional Research Center, United States Department of Agriculture, 1815 North University Street, Peoria, Ill. 61604, U.S.A., where it was assigned accession number NRRL 18085. The characteristics of strain AB 718C-41 are given in the Journal of Antibiotics, 1987, p. 567-574 and U.S. Pat. No. 4,918,174.

Additional microorganisms capable of producing Tiacumicins include mutant species, which show advantageous properties compared with species known in the art. Such bacterial strains can be generated by mutagenesis of a parent strain. Strategies and methods of mutagenesis, procedures for screening and isolation of mutated bacterial strains, compositions of media used in producing the mutant strains of the invention are known in the art. Microorganisms designated as strains may embody advantages such increased production of desired macrolide, more efficient usage of nutrient media, or decreased requirement of oxygen for aerobic growth.

In the preferred embodiment, cultivation of *Dactylosporangium aurantiacum* subspecies *hamdenensis* AB 718C-41 NRRL 18085 for the production of the Tiacumicins is carried out in a medium containing readily assimilable carbon sources, nitrogen sources, inorganic salts and other organic ingredients with one or more absorbents under proper aeration conditions and mixing in a sterile environment. Compositions of nutrient media used in producing antibiotics of the invention will be described in detail in the examples.

Carbon sources capable of supporting microorganism growth include but are not limited to glucose, sucrose, galactose, fructose, starch, molasses, malt extracts, dextrins, whey, glycerol, lipids, corn meal and the like and combinations thereof. According to one embodiment of the invention, the carbon source is present in the range between 0.2-10% by weight. Amounts of carbon sources according to one embodiment of the invention are given in Table 2.

Nitrogen sources capable of supporting microorganism growth include but are not limited to beef extract, soybean meal, cottonseed meal, whole yeast, yeast extract, soybean flour, peptone, casamino acid, fish powder, corn steep liquor, ammonium salts, casein, amino acids and the like and combinations thereof. According to one embodiment of the present invention, the nutrient medium contains fish powder (999 Prime quality fishmeal, TripelNine Fish Protein, a.m.b.a. Fiskerihavnsgade 35, 6700 Esbjerg, Demark) as the nitrogen source. According to one embodiment of the invention, the nitrogen source is present in the range between 0.1-5.0% by weight. Amounts of nitrogen sources according to one embodiment of the invention are given in Table 2.

Essential trace elements necessary for the growth and development of the organism may occur as impurities in other constituents of the media in amounts sufficient to meet the growth and biosynthetic requirements of the organism. However, it may be beneficial to incorporate in the culture media additional soluble nutrient inorganic salts capable of assisting microorganism growth. Inorganic salts capable of supporting microorganism growth include but are not limited to $K_2HPO_4$, $MgSO_4.7H_2O$, KCl, $CaCO_3$ and the like. Essential trace elements are preferably present in the range between 0.02-2.0% by weight. Amounts of individual essential elements according to one embodiment of the invention are given in Table 2.

Commercially available adsorbent resins were found to enhance the yield and recovery efficiency of Tiacumicins during the fermentation. Such adsorbents include but are not limited to Amberlite® XAD16, XAD16HP, XAD2, XAD7HP, XAD1180, XAD1600, and IRC50 (all Rohm & Haas Co., U.S.A.), Duolite® XAD761 (Rohm & Haas Co., U.S.A.) and the like. Adsorbents are preferably present in the range between 0.5-15% by weight. Amounts of adsorbents according to one embodiment of the invention are given in Table 2.

As is customary in aerobic submerged culture processes, sterile air is dispersed through the culture medium. The oxygen concentration was kept at higher than 3% (InPro 6000 series $O_2$ sensors, Mettler Toledo). Under these conditions the growth of cells is maintained at a level that prevents the growth conditions becoming anaerobic. In some embodiments, the limiting component is chosen from a carbon source, nitrogen source, or any other component required by the cells (e.g., in the feed medium).

Bacteria are grown under suitable growth conditions. Such suitable growth conditions are characterized by limiting the availability of a component of the growth medium and/or feed medium in such a way that aerobic conditions for the growth of said bacterium are maintained. Such conditions can be also characterized e.g. by maintaining a level of dissolved oxygen at a concentration between about 2% to 30%. Such levels of dissolved oxygen can vary depending on the specific technical equipment used for growing bacteria and for measuring the dissolved oxygen concentration.

Tiacumicin-producing bacteria can be grown in vessels ranging from shake flasks to large "batch" fermenters, by methods known in the art. For producing substantial quantities of Tiacumicins, submerged aerobic fermentation in tanks is utilized. However, small amounts may be obtained by shake-flask culture. For tank fermentation, it is preferable to use a vegetative inoculum. The vegetative inoculum is prepared by inoculating a small volume of culture medium with the spore form, mycelial fragments, or a lyophilized pellet of the organism to obtain a fresh, actively growing culture of the organism. The vegetative inoculum is then transferred to a larger tank where, after a suitable incubation time, the Tiacumicin antibiotic is produced in much improved yield.

It may be necessary to add small amounts of an antifoam agent to large-scale fermentation media if foaming becomes a problem.

The production proceeds in a control medium with other additives/ingredients to improve the production. A liquid-submerged, stirred-culture process is used for the production of Tiacumicins. Fermentation is carried out at a temperature range of 25° C. to 37° C. The consumption of the carbon source is carefully monitored and an additional amount of carbon source is added as needed. The pH of the fermentation is preferably maintained between about 6.0 to about 8.0. Tiacumicin B is produced and accumulated between 3 to 15 days after inoculation of the fermentation. The standard control medium consists of the following ingredients in the following quantities:

| | |
|---|---|
| Fish powder | 0.1% to 5% |
| Glucose | 0.2% to 10% |

-continued

| | |
|---|---|
| $K_2HPO_4$ | 0.02% to 0.5% |
| $MgSO_4.7H_2O$ | 0.02% to 0.5% |
| KCl | 0.01% to 0.3% |
| $CaCO_3$ | 0.1% to 2% |

Other additives/ingredients consist of:

| | |
|---|---|
| Casamino acid | 0.05% to 2%, |
| Yeast extract | 0.05% to 2% |
| XAD-16 resin | 0.5% to 15% |

Upon completion of fermentation, the solid mass (including the adsorbent resin) is separated from the broth by sieving. Tiacumicins are eluted from the resin with organic solvents such as ethyl acetate, methanol, acetonitrile or a mixture of two or more organic solvents. The extract is then concentrated under reduced pressure. This residue is further purified by trituration with low polarity solvents such as hexanes, heptanes, methylcyclohexane, or by partitioning between two phase solvent systems such as: ethyl acetate/water; ethyl acetate/aqueous sodium chloride solution; methanol/hexane, acetonitrile/hexane or other mixtures of two or more solvents in various ratios and combinations or by Sephadex column chromatography eluting with an appropriate organic solvent system. If needed, Tiacumicins can be further purified either by crystallization, and/or chromatographic separation and/or High-Performance Liquid Chromatography (HPLC) and/or liquid/liquid partitioning and/or trituration.

EXAMPLES

As can be appreciated from the disclosure above, the present invention has a wide variety of applications. Accordingly, the following examples are offered by way of illustration, not by way of limitation.

Example 1

*Dactylosporangium aurantiacum* subsp. *hamdenensis* AB 718C-41 NRRL 18085 (−20° C. stock), was maintained on 1 mL of Medium No. 104 (Table 1). After standard sterilization conditions (30 min., 121° C., 1.05 kg/cm$^2$) the seed flask (250 mL) containing Medium No. 104 (50 mL) was inoculated with AB 718C-41 NRRL 18085 on a shaker (set @ 250 rpm) at 30° C. for 72 hr. Five percent vegetative inoculum from the first passage seed flask was then transferred aseptically to a fermentation flask containing the same ingredients as in Table 1.

TABLE 1

Ingredients of Medium No. 104

| Fish powder | Glucose | $K_2HPO_4$ | $MgSO_4.7H_2O$ | KCl | $CaCO_3$ | Casamino acid | Yeast extract | XAD-16 |
|---|---|---|---|---|---|---|---|---|
| 10 g/L | 20 g/L | 0.5 g/L | 0.5 g/L | 0.3 g/L | 3 g/L | 2.5 g/L | 2.5 g/L | 20 g/L |

Fermentation flasks were incubated on a rotary shaker at 30° C. for 3 to 12 days. Samples of the whole culture fermentation broth were filtered. The filter cake was washed with MeOH and solvents were removed under reduced pressure. The residue was re-constituted in methanol to the same volume of the original fermentation broth. Analysis was performed using a Waters BREEZE HPLC system coupling with Waters 2487 2-channel UV/Vis detector. Tiacumincins were assayed on a 50×4.6 µm I.D., 5 µm YMC ODS-A column (YMC catalog # CCA AS05-0546WT) with a mobile phase consisting of 45% acetonitrile in water containing 0.1% phosphoric acid at a flow rate of 1.5 mL/minute. Tiacumicins were detected at 266 nm. An HPLC chromatogram of a crude product (Tiacumicin B retention time @ 12.6 minutes) is shown in FIG. 1. In this example the crude yield of Tiacumicin B was about 250 mg/L after 7 days. After purification by HPLC, the yield of Tiacumicin B was about 100 mg/L.

Example 2

After standard sterilization conditions (30 min, 121° C., 1.05 kg/cm$^2$) the seed flask (250 mL) containing Medium No. 104 (50 mL) was inoculated with AB 718C-41 NRRL 18085 and incubated on a shaker (set @ 250 rpm) at 30° C. for 72 hr. Five percent vegetative inoculum from the first passage seed flask was transferred aseptically to a seed flask containing the same ingredients as in Table 1 and was incubated on a rotary shaker at 30° C. for 72 hr. Five percent inoculum from the second passage seed flasks was then used to inoculate with AB 718C-41 NRRL 18085 in a 5-liter fermenter containing Medium No. 104 (2.5 L). Excessive foam formation was controlled by the addition of an antifoaming agent (Sigma A-6426). This product is a mixture of non-silicone organic defoamers in a polyol dispersion.

Glucose consumption was monitored as a growth parameter and its level was controlled by the addition of the feeding medium. Feeding medium and conditions in Example 2 were as follows:
Feeding medium:

| Yeast extract | Casamino acid | Glucose | K$_2$HPO$_4$ | MgSO$_4$.7H$_2$O | KCl |
|---|---|---|---|---|---|
| 1.5% | 1.5% | 30% | 0.5% | 0.5% | 0.3% |

Figure 2:
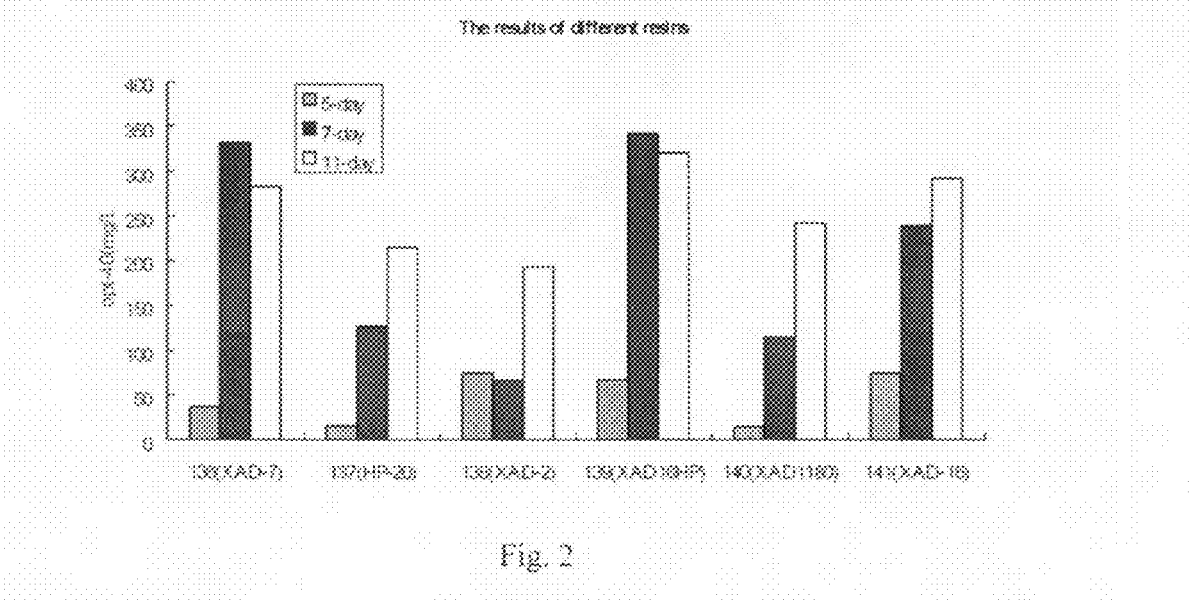
FIG. 2 shows an HPLC chromatogram of fermentation products produced according to Example 2; Tiacumicin B has a retention time of approximately 11.8 min.
Figure 3:
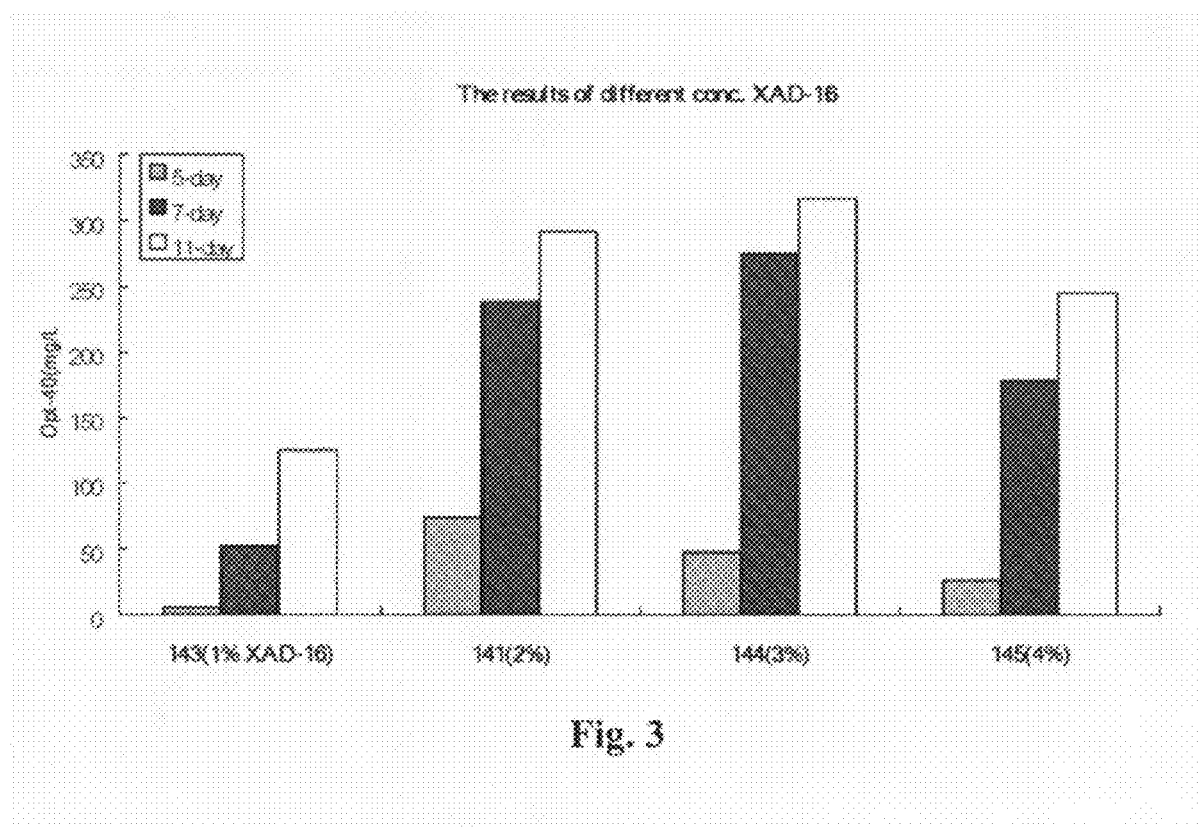
FIG. 3 shows an HPLC chromatogram of purified (by HPLC) Tiacumicin B produced by fermentation according to Example 2; Tiacumicin B has a retention time of approximately 12.0 min.

Fermenter Medium: No. 104
Fermenter Volume: 5 liters
Sterilization: 40 minutes, 121° C., 1.05 kg/cm$^2$
Incubation Temperature: 30° C.
Aeration rate: 0.5-1.5 volumes of air per culture volume and minute
Fermenter Agitation: 300-500 rpm The fermentation was carried out for 8 days and the XAD-16 resin was separated from the culture broth by sieving. After washing with water the XAD-16 resin was eluted with methanol (5-10× volume of XAD-16). Methanol was evaporated and the oily residue was extracted three times with ethyl acetate. The extracts were combined and concentrated under reduced pressure to an oily residue. The oily residue was dried and washed with hexane to give the crude product as a pale brown powder and its HPLC chromatogram (Tiacumincin B retention time @ 11.8 minutes) is shown in FIG. 2. This was purified by silica gel column (mixture of ethyl acetate and hexane as eluent) and the resultant material was further purified by RP-HPLC (reverse phase HPLC) to give Tiacumicin B as a white solid. The purity was determined to be >95% by HPLC chromatography and the chromatogram (Tiacumincin B retention time @ 12.0 minutes) is shown in FIG. 3. Analysis of the isolated Tiacumincin B gave identical $^1$H and $^{13}$C NMR data to those reported in J. Antibiotics, 1987, 575-588, and these are summarized below.

Tiacumicin B:
mp 129-140° C. (white powder from RP-HPLC);
mp 166-169° C. (white needles from isopropanol);
$[\alpha]_D^{20}$ −6.9 (c 2.0, MeOH);
MS m/z (ESI) 1079.7(M+Na)$^+$;
$^1$H NMR (400 MHz, CD$_3$OD) δ 7.21 (d, 1H), 6.59 (dd, 1H), 5.95 (ddd, 1H), 5.83 (br s, 1H), 5.57 (t, 1H), 5.13 (br d, 1H), 5.09 (t, 1H), 5.02 (d, 1H), 4.71 (m, 1H), 4.71 (br s, 1H), 4.64 (br s, 1H), 4.61 (d, 1H), 4.42 (d, 1H), 4.23 (m, 1H), 4.02 (pentet, 1H), 3.92 (dd, 1H), 3.73 (m, 2H), 3.70 (d, 1H), 3.56 (s, 3H), 3.52-3.56 (m, 2H), 2.92 (m, 2H), 2.64-2.76 (m, 3H), 2.59 (heptet, 1H), 2.49 (ddd, 1H), 2.42 (ddd, 1H), 2.01 (dq, 1H), 1.81 (s, 3H), 1.76 (s, 3H), 1.65 (s, 3H), 1.35 (d, 3H), 1.29 (m, 1H), 1.20 (t, 3H), 1.19 (d, 3H), 1.17 (d, 3H), 1.16 (d, 3H), 1.14 (s, 3H), 1.12 (s, 3H), 0.87 (t, 3H); $^{13}$C NMR (100 MHz, CD$_3$OD) δ 178.4, 169.7, 169.1, 154.6, 153.9, 146.2, 143.7, 141.9, 137.1, 137.0, 136.4, 134.6, 128.5, 126.9, 125.6, 124.6, 114.8, 112.8, 108.8, 102.3, 97.2, 94.3, 82.5, 78.6, 76.9, 75.9, 74.5, 73.5, 73.2, 72.8, 71.6, 70.5, 68.3, 63.9, 62.2, 42.5, 37.3, 35.4, 28.7, 28.3, 26.9, 26.4, 20.3, 19.6, 19.2, 18.7, 18.2, 17.6, 15.5, 14.6, 14.0, 11.4.

Example 3

A crude sample of Tiacumicin B (15 g) was obtained by fermentation as an oily residue after release from the resin as described in Example 2. This was dissolved in ethyl acetate (300 mL) at 35° C. and the solution was shaken in a separatory funnel with water (300 mL) and allowed to settle for 1 minute. Saturated aqueous sodium chloride solution (100 mL) was added and the mixture was allowed to stand for a further 1 minute. The lower phase and any solids present at the interface were discarded and the upper phase was concentrated to a brown solid under reduced pressure at 35° C. The resulting foam was subjected to reverse phase medium pressure liquid chromatography using a Biotage 75 L apparatus coupled to an Isco UA-6 UV/vis detector with the following parameters:
Column: 1.2 kg, Biotage KP-C18-HS silica.
Equilibration: 50:50:1, MeCN/H$_2$O/AcOH (6 L).
Loading: In methanol (20 mL) via sample injection module containing 25 g of Biotage KP-C18-HS silica.
Eluent: 50:50:1, MeCN/H$_2$O/AcOH.
Flow: 230 mL/min
Pressure: Solvent—90 psi
    Radial—100 psi
Detector: Wavelength—254 nm
    Path length—0.1 cm
    Sensitivity—2
    Chart speed—60 cm/hr.
    Noise filter—5 sec.
Fraction Collection: Manual—began collection just after inflection between main peak and previous peak, ended collection at 20% of main peak height.
Column Conditioning: 100% MeCN (4 L)

Saturated aqueous sodium chloride solution (25% of the fraction volume) was added to the collected fraction. The mixture was shaken and allowed to separate into two phases. The upper phase was removed and concentrated to dryness under reduced pressure at 30° C. The resulting solid was dissolved in ethyl acetate (75 mL) and washed with water (2×75 mL) to remove sodium chloride. The organic phase was concentrated under reduced pressure at 30° C. to a yellow foam (recovery: 4.56 g, 30%; purity ~93%).

Figure 4:
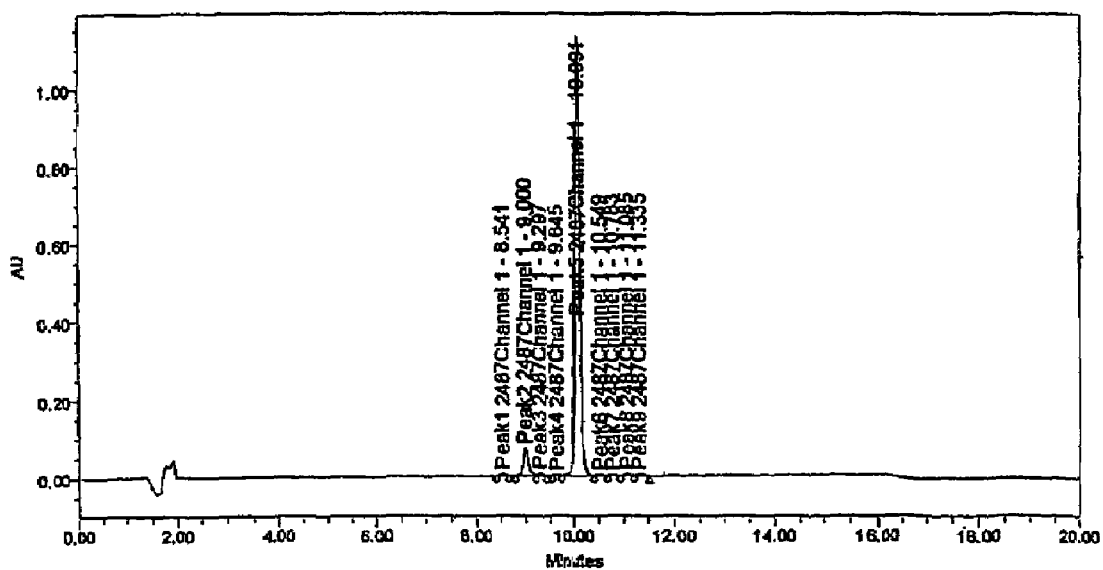
FIG. 4 shows an HPLC chromatogram of Tiacumicin B produced by fermentation and purified by reverse phase medium pressure liquid chromatography followed by trituration according to Example 3; Tiacumicin B has a retention time of approximately 10.1 min.
Figure 3:
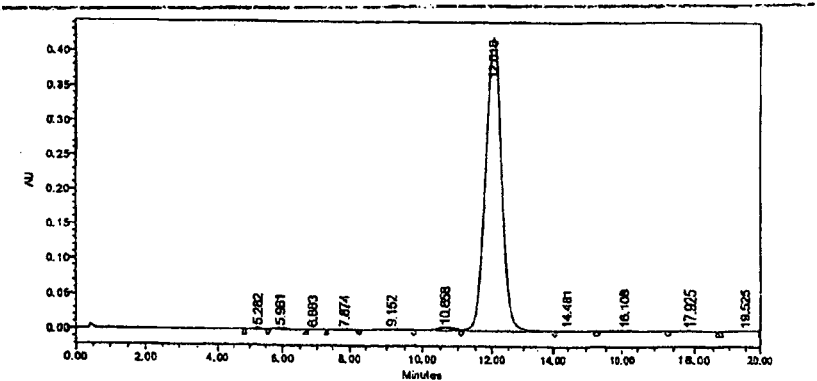

The material was combined with several other batches (total: 156.0 g, 90.8% purity) and to this was added isopropanol (1000 mL). The mixture was sonicated with stirring at room temperature for 20 min. to produce an off-white suspension. At this point the material was filtered and the filter cake was washed with isopropanol (300 mL). The solid was dried under high vacuum to leave an off white powder (recovery: 146.2 g, 94%; purity: 91.1%) (FIG. 4). Mp 156-160° C.; $[\alpha]_D^{20}$ −8.4 (c 2.0, MeOH); MS m/z (ESI) 1079.7(M+Na)$^+$; Calcd for $C_{52}H_{74}Cl_2O_{18}$: C, 59.03; H, 7.05; Cl, 6.70. Found: C, 58.75; H, 7.04; Cl, 6.91.

The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein. In addition, where features or aspects of an invention are described in terms of the Markush group, those schooled in the art will recognize that the invention is also thereby described in terms of any individual member or subgroup of members of the Markush group.

It is to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications, are incorporated herein by reference.

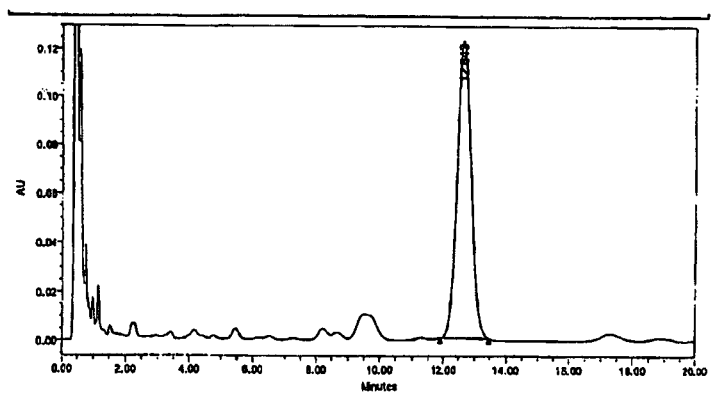
Figure 2
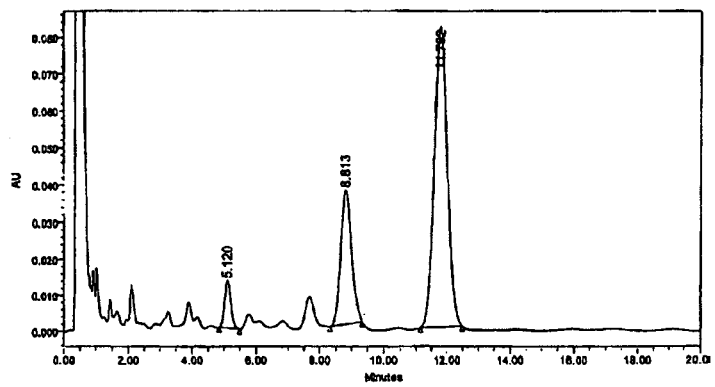

We claim:

1. A process for producing tiacumicin B comprises:
culturing a microorganism in a nutrient medium to accumulate the tiacumicin B in the nutrient medium; and
isolating the tiacumicin B from the nutrient medium;
wherein the nutrient medium comprises 0.5%-15% by weight of an adsorbent resin capable of absorbing the tiacumicin B.

2. The process of claim 1 wherein the adsorbent resin is selected from the group consisting of Amberlite® XAD16, XAD16HP, XAD2, XAD7HP, XAD1180, XAD1600, IRC50, Duolite® XAD761 and a reverse phase silica gel.

3. The process of claim 1 wherein the microorganism is *Dactylosporangium aurantiacum* subspecies *hamdenensis* NHRL 18085.

4. The process of claim 1 wherein the isolating step is conducted by at least one of following methods: 1) sieving and removing undesired material by eluting with at least one solvent or a solvent mixture; 2) extraction with at least one solvent or a solvent mixture; 3) crystallization; 4) chromatographic separation; 5) High-Performance Liquid Chromatography (HPLC); 6) MPLC; 7) trituration; and 8) extraction with saturated brine with at least one solvent or a solvent mixture.

5. The process of claim 1 wherein the culturing step is conducted at a temperature from about 25 to about 35° C. and at a pH from about 6 to about 8.

6. The process of claim 1 wherein the nutrient medium comprises one or more carbon sources selected from the group consisting of glucose, sucrose, starch, molasses, dextrins, whey, glycerol, lipids, and corn meal.

7. The process of claim 1 wherein the nutrient medium is fed with an additional carbon source as needed.

8. The process of claim 1 wherein the nutrient medium comprises one or more inorganic salts selected from the group consisting of $K_2HPO_4$, $MgSO_4$, $7H_2O$, and $CaCO_3$.

9. The process of claim 1 wherein the nutrient medium comprises one or more nitrogen/organic sources selected from the group consisting of beef extract, soybean meal, whole yeast, yeast extract, soybean flour, peptone, casamino acid, fish powder, corn steep liquor, ammonium salts, casein, and amino acids.

10. The process of claim 2 wherein the reverse phase silica gel is selected from the group consisting of KP-C18, KP-C18-WP and KP-C18HS.

* * * * *

UNITED STATES PATENT AND TRADEMARK OFFICE
CERTIFICATE OF CORRECTION

PATENT NO. : 7,507,564 B2  Page 1 of 1
APPLICATION NO. : 10/520863
DATED : March 24, 2009
INVENTOR(S) : Youe-Kong Shue It is certified that error appears in the above-identified patent and that said Letters Patent is hereby corrected as shown below:

Title Page Item (60) Related US Application Data should read

--60/399,956   07/29/2002 ABN--

On the Title page Item [60] should read

--Benefit of priority under 35 U.S.C. 119(e) is claimed herein to U.S. Provisional application No. 60/399,956, filed July 29, 2002 and International Application No. PCT/US2003/021977 filed 15 July 2003. The disclosures of the above-reference applications are incorporated by reference in their entirety herein.--

In the Specification

In column 1, line 1, after the title "Tiacumicin Production," please add:

--FIELD OF INVENTION

The invention relates generally to fermentation production of antibiotics and to media used in the same.--

Signed and Sealed this

Ninth Day of June, 2009

JOHN DOLL
*Acting Director of the United States Patent and Trademark Office*

UNITED STATES PATENT AND TRADEMARK OFFICE
CERTIFICATE OF CORRECTION

| | |
|---|---|
| PATENT NO. | : 7,507,564 B2 |
| APPLICATION NO. | : 10/520863 |
| DATED | : March 24, 2009 |
| INVENTOR(S) | : Youe-Kong Shue |

It is certified that error appears in the above-identified patent and that said Letters Patent is hereby corrected as shown below:

In the Drawings

Figs. 1, 2 and 3 should be replaced with the corrected Figs. 1, 2 and 3 as shown on the attached pages.

Signed and Sealed this
Fourth Day of September, 2012

David J. Kappos
*Director of the United States Patent and Trademark Office*